United States Patent [19]
Ratnasamy et al.

[11] Patent Number: 5,932,773
[45] Date of Patent: Aug. 3, 1999

[54] PROCESS FOR THE PREPARATION OF α AND β NAPTHOL BY HYDROXYLATION OF NAPHTHALENE USING ORGANOTRANSITION METAL COMPLEX

[75] Inventors: Paul Ratnasamy; Robert Raja; Pramod Prabhakar Moghe; Madhav Gopal Kotasthane; Ashwini Vinayak Pol; Prakash Kondiba Bahirat, all of Maharashtra, India

[73] Assignee: Council of Scientific & Industrial Research, India

[21] Appl. No.: 08/829,400

[22] Filed: Mar. 31, 1997

[51] Int. Cl.$^6$ ..................................................... C07C 37/00
[52] U.S. Cl. ................................................................ 568/741
[58] Field of Search ..................................... 568/735, 741, 568/742

[56] References Cited

PUBLICATIONS

Carrier et al., Tetrathedron Lett., (1990), 31(46), 6645–8.
Diddams, Inorganic supports and catalysts in Solid Supports and Catalysts in Organic Synthesis, K. Smith, ed., 1993.

*Primary Examiner*—Michael L. Shippen
*Attorney, Agent, or Firm*—Londa and Traub LLP

[57] ABSTRACT

This invention relates to a process for the hydroxylation of napthalene to and β naphthols which comprises reacting napthalene with hydrogen peroxide in the presence of a solid catalyst containing an organotransition metal complex wherein some or all of the hydrogen atoms of the said organotransition metal complex have been substituted by one or more electron withdrawing group in the presence of solvents, with or without promoter and isolating the naphthols formed by conventional methods.

5 Claims, No Drawings

PROCESS FOR THE PREPARATION OF α AND β NAPTHOL BY HYDROXYLATION OF NAPHTHALENE USING ORGANOTRANSITION METAL COMPLEX

FIELD OF THE INVENTION

This invention relates to a process for the preparation of a mixture of α naphthol and β naphthol by the hydroxylation of napthalene. More particularly, the present invention relates to an improved process for the preparation of a mixture of naphthol and β naphthol by the hydroxylation of napthalene, using hydrogen peroxide as the oxidant and a solid organotransition metal complex as a catalyst.

In terms of quantity and scope of application, α naphthol and β naphthol have found wide application in the field of plasticisers, resin manufacture, dyes and intermediates, medicinal organics, synthetic perfumes and anti-oxidants.

PRIOR ART REFERENCES OF THE INVENTION

Two routes have gained industrial importance for the production of β naphthol, namely alkali fusion of sodium 2-sulphonate and the oxidative cleavage of 2-isopropyl napthalene. In alkali fusion, napthalene is transformed to napthalene 2-sulphonic acid at 160° C., under thermodynamically controlled conditions and converted to its sodium salt by the alkali. This salt on hydrolysis yields β naphthol.

In the 2-isopropyl napthalene process, 2-isopropyl napthalene is obtained by reacting propylene and napthalene at a temperature between 150–240° C. and a pressure of 10 bar. The introduction of air at 110° C. produces a hydroperoxide of the 2-isomer. The hydroperoxide cleaves with sulphuric acid to yield β naphthol and acetone. α-naphthol is also produced like β-naphthol via caustic fusion of naphthalene-1-sulphonic acid. The I.G. Farbenindustrie process for α-naphthol involves hydrolysis of α-napthylamine with 22% sulphuric acid at 200° C. under pressure. Union Carbide developed a process for α-naphthol based on catalytic oxidation of tetralone to tetralol followed by dehydrogenation to yield α-naphthol.

There have been many references in the prior art, but of particular interest with respect to the present invention are processes in which aromatic compounds are hydroxylated using hydrogen peroxide as the oxidant. U.S. Pat. No. 3,914,324 describes a process in which phenol is hydroxylated with hydrogen peroxide in the presence of alkanoic acid and an acid catalyst such as phosphoric acid or trichloro acetic acid. U.S. Pat. No. 3,662,006 describes a process where benzene and phenol are hydroxylated by hydrogen peroxide using iron, chromium and nickel as the catalyst to get a mixture of hydroxybenzenes. U.S. Pat. No. 3,931,295 describes the hydroxylation of aromatic compounds with hydrogen peroxide containing a salt of hydrocyanic acid or an aliphatic nitrile compound. U.S. Pat. No. 3,953,527 describes the hydroxylation of aromatics with hydrogen peroxide in the presence of phosphorous compounds. U.S. Pat. No. 3,985,797 describes a process in which aromatics are hydroxylated with hydrogen peroxide at –10° C. to 100° C. and a pressure of about 100 atmospheres in the presence of an alkaline solution of hydrocyanic acid. U.S. Pat. No. 3,890,397 describes the hydroxylation of 1,2 dihydro napthalene with 1,2,3,4 tetrohydronapthalene-1-hydroperoxide. U.S. Pat. No. 4,301,307 describes the hydroxylation of aromatics with hydrogen peroxide in the presence of triflouro methane sulphonic acid. U.S. Pat. No. 4,396,783 describes regio-selective hydroxylation of napthalene using hydrogen peroxide and Lewis or superacidic mixtures thereof. German Patent DE 3,102,305 describes a process for the preparation of naphthol and β naphthol with high isomer selectivity, with large excess of hydrogen peroxide and in the presence of acid systems like HF, HF-$BF_3$ and $FSO_3H$.

There are many drawbacks in existing process mentioned hereinabove and in commercial practice worldwide, extensively.

One major drawback in alkali fusion process to produce α and β naphthol is the requirement of thermodynamical control during sulphonation of naphthalene to yield in major proportion of the isomer napthalene-1 sulphonic acid for α naphthol and napthalene-2 sulphonic acid for β naphthol. The other drawback is that the process cannot be termed as "Environment-friendly" which involves hazardous steps like sulphonation, alkali fusion, hydrolysis of the sodium salt with acid and finally generation of side products in the process and requires expensive waste treatment for air and water pollution.

In the other commercial process of β naphthol from 2-isopropylnapthalene drawback involves hazardous reaction conditions like reaction of propylene with napthalene at 150°–240° C. under pressure to yield selectively 2-isopropylnapthalene, then to produce hydroperoxide of the 2-isopropylnapthalene isomer at 110° C. with air or oxygen, further cleavage of the hydroperoxide with acid. The process also poses waste disposal problems along with side products.

Drawbacks in the α naphthol process from tetralone are main requirement for hydrogenation is that napthalene should be free from sulphur. Second drawback is the involvement of hazardous steps like hydroperoxide generation of tetralene to 1-tetralol and two stage catalytic hydrogenation at the temperature ranging from 200°–400° C. to yield α naphthol.

The drawbacks of other hydroxylation processes mentioned in the literature are the hazardous reaction conditions of the processes, use of expensive corrosive liquid catalysts like HF $CF_3COOH$, HF complexes, use of drastic conditions e.g. reaction at –10° C. to –70° C. and finally poor conversion to the hydroxylation products.

It is thus evident that there is a need for the development of a process for the hydroxylation of napthalene to β naphthol and α naphthol in significant yields and using solid recyclable catalyst and operating at low enough temperature (below 100° C.) to minimise production of side products avoiding hazardous reaction conditions.

SUMMARY OF THE INVENTION

Therefore, the present invention provides a process for the preparation of α and β naphthol by the hydroxylation of napthalene using a catalyst which would remain in the solid state at the end of hydroxylation reaction thereby facilitating the easy separation, recovery and recycle of catalyst from the reaction products without having any adverse impact on the environment.

OBJECTS AND DETAILED DESCRIPTION OF THE INVENTION

The main object of the present invention is to provide a process for the hydroxylation of napthalene to naphthols, which comprises reacting napthalene with hydrogen peroxide in the presence of a solid catalyst consisting of an organotransition metal complex wherein some or all of the hydrogen atoms of the said organotransition metal complex have been substituted by one or more electron withdrawing groups, at a temperature in the range of 20° C. to 80° C., in the presence of solvents, with or without a promoter and isolating the naphthols formed by conventional methods.

Another object of the present invention is to provide a process whereby the yield of β naphthol should be higher, selective in the prior art processes.

Yet another objective of the present invention is to provide an improved process for the preparation of β naphthol and α naphthol at reaction conditions wherein large number of byproducts such as phthalic anhydride, napthoquinone are generated during hydroxylation of napthalene.

Pthalocyanines consist of large, planar, conjugated, ring systems which serve as tetradentate ligands. Metalic cations can be easily accommodated at the center of these systems with the four nitrogens as the ligating atoms. Metal containing pthalocyanine compounds are known to be useful as chemical reagents of a catalytic nature, more particularly in directing certain oxidative processes. Many known pthalocyanines have been judged to suffer certain drawbacks by being deficient in the combination of properties desired for many candidate uses, such as in the oxidation of alkanes and more particularly in the oxidation of napthalene. One major drawback of homogeneous pthalocyanine catalysts in industrial oxidation processes is the formation of aggregates in solution which significantly deactivates these catalysts.

Due to the continued research in this area, the applicants observed that the organotransition metal complexes used as catalysts are solids insoluble in napthalene or the reaction products arising from oxidation of napthalene. Hence, they do not undergo aggregation or change of phase during the oxidation wherein such changes are known to lead to catalyst deactivation problems.

Another drawback of pthalocyanines used in the prior art as catalysts for alkane oxidation is their low oxidative stability which is due to the easy oxidizability of the hydrogen atoms attached to the nucleus of the pthalocyanines.

The applicants have found that the oxidative stability as well as the catalytic activity of the metal pthalocyanines used as catalysts in the hydroxylation of napthalene are enhanced by replacing the hydrogens from the pthalocyanines by electron withdrawing groups like the halogens, nitro or cyano groups thereby rendering the metal ions easier to reduce leading to an improved oxidation activity and stability of the catalysts during the reaction.

There are a total of 16 hydrogen atom positions on such pthalocyanine molecules which can in principle, be substituted by other substituents. The applicants have observed that when some or all of the hydrogen atoms of the said pthalocyanines are substituted by one or more electron withdrawing groups such as halogen, nitro or cyano groups or mixtures of such groups there is substantial improvement in selectivity and conversion to yield naphthols.

Accordingly, the present invention provides an improved process for the hydroxylation of napthalene to naphthols which comprises reacting napthalene with hydrogen peroxide in the presence of a solid catalyst consisting of an organotransition metal complex wherein some or all of the hydrogen atoms of the said organotransition metal complex have been substituted by one or more electron withdrawing groups, at a temperature in the range of 20° C. to 80° C., in the presence of solvents, with or without a promoter and isolating the naphthols formed by conventional methods.

In an embodiment of the present invention the organotransition metal complex is selected from pthalocyanines and porphyrins.

In another embodiment of the present invention, the transition metal is selected from iron, cobalt, copper, chromium, manganese or mixtures thereof.

Preferably, the hydroxylating agent used is hydrogen peroxide having the strength of 28 to 90% w/v.

Some nonlimiting examples of such organo transition metal complexes used as catalysts in the hydroxylation of napthalene to naphthols are iron halopthalocyanines, copper halo pthalocyanines, cobalt halo pthalocyanines, chromium halo pthalocyanines, manganese halo pthalocyanines, iron nitro pthalocyanines, copper nitro pthalocyanines, chromium nitro pthalocyanines, cobalt nitro pthalocyanines, manganese nitro pthalocyanines, manganese cyano pthalocyanines, copper cyano pthalocyanines and chromium cyano pthalocyanines.

In still another embodiment of present invention, the electron withdrawing groups attached to the organotransition metal complex is selected from the halogens, fluorine, chlorine, bromine or iodine or the nitro or cyano groups.

In a preferred embodiment of the present invention, the hydroxylation of napthalene is catalysed by the halogen, cyano or nitro pthalocyanines of the metals iron, cobalt, copper, chromium, manganese or mixtures thereof.

In yet another embodiment of the present invention, the above mentioned hydroxylation reaction can be carried out in the presence or absence of solvents. It may be an advantageous option to carry out the said oxidation reaction in the presence of a suitable solvent which would maintain the hydroxylation products like naphthols in the dissolved state during the course of the reaction, thereby facilitating the separation of the said naphthols from the solid catalysts. Suitable solvents for such use include acetonitrile, methanol, water, butanol and cyclohexanol. Examples of such solvents which can be used in the process of the present invention include acetonitrile, acetone, benzene or any other organic solvent which is inert under the hydroxylation reaction conditions.

In another advantageous embodiment of the present invention, the organotransition metal complex may be encapsulated in a solid matrix. Due to the greater dispersion of the organotransition metal complex catalyst in solid matrices and the consequent enhanced stability of the structural integrity of the catalyst significant process advantages like greater activity, stability and easy recovery and recyclability of the catalyst are observed. Examples of such solid matrices include inorganic oxide like silica, alumina, molecular sieves, zeolites and the like as well as organic polymeric material.

It is an advantageous feature of the process of the present invention that due to the high activity the catalysts used herein, the hydroxylation reaction can be carried out at temperatures much below those used in the prior art and preferably below 80° C., thereby leading to much lower yields of undesired side products like pthalic anhydride, napthoquinone.

The details of the present invention is described in the examples given below which are provided by way of illustration only and therefore should not be construed to limit the scope of the invention.

EXAMPLE-1

In a 250 ml 4 necked flask fitted with stirrer, condenser, thermometer, addition funnel in an electrically heated oil bath was charged with 0.5 g of solid copper tetra deca chloro pthalocyanine zeolite catalyst, acetonitrile 50 ml (39 g) and napthalene 12.8 g, hydrogen peroxide 13.6 ml (28%) (3.808 g) was slowly added dropwise at 50° C. to the reaction mixture under stirring in 15 minutes. The reaction was continued at 80° C. for 5 hrs. The reaction mixture was then cooled and separated from solid catalyst by filtration and analysed by gas chromatography (Shimadzu GC RIA) using carbowax column and flame ionisation detecter (FID). The identify of the product was confirmed by GC mass spectroscopy (Shimadzu GCMS-QP 2000A).

The conversion of napthalene was 22.3%

The conversion of β naphthol was 20.12%

The other side products were napthaquinone 0.3%, pthalic anhydride 1% and α naphthol 0.7%

EXAMPLE-2

In a 250 ml 4 necked flask fitted with stirrer, condenser, thermometer, addition funnel in an electrically heated oil bath was charged with 0.5 g of solid copper tetra deca chloro pthalocyanine zeolite catalyst, methanol 150 ml (118 g) and napthalene 12.8 g, hydrogen peroxide 13.6 ml (28%) (3.808 g) was slowly added dropwise at 50° C. to the reaction mixture under stirring in 15 minutes. The reaction continued at 80° C. for 5 hrs. The reaction mixture was then cooled and separated from solid catalyst by filtration and analysed by gas chromatography (Shimadzu GC RIA) using carbowax column and flame ionisation detecter (FID). The identify of the product was confirmed by GC mass spectroscopy (Shimadzu GCMS-QP 2000A) using standard compounds.

The conversion of napthalene was 6.5%

The conversion of β naphthol was 4.9%

EXAMPLE-3

In a 250 ml 4 necked flask fitted with stirrer, condenser, thermometer, addition funnel in an electrically heated oil bath was charged with 0.5 g of solid copper tetra deca chloro pthalocyanine zeolite catalyst, acetonitrile 50 ml. (39 g) and napthalene 12.8 g, hydrogen peroxide 13.6 ml (28%) (3.808 g) was slowly added dropwise at 50° C. to the reaction mixture under stirring in 15 minutes. The reaction continued at 80° C. for 5 hrs. The reaction mixture was then cooled and separated from solid catalyst by filtration and analysed by gas chromatography (Shimadzu GC RIA) using carbowax column and flame ionisation detecter (FID). The identify of the product was confirmed by GC mass spectroscopy (Shimadzu GCMS-QP 2000A) using standard compounds.

The conversion of napthalene was 15.8%

The conversion of β naphthol was 6.88%

The other side products were napthaquinone 1.28%, pthalic anhydride 4% and α naphthol 1.45%.

EXAMPLE-4

In a 250 ml 4 necked flask fitted with stirrer, condenser, thermometer, addition funnel in an electrically heated oil bath was charged with 0.5 g of solid copper tetra deca chloro pthalocyanine zeolite catalyst, acetonitrile 50 ml (39 g) and napthalene 12.8 g, hydrogen peroxide 13.6 ml (28%) (3.808 g) was slowly added dropwise at 50° C. to the reaction mixture under stirring in 15 minutes. The reaction continued at 80° C. for 5 hrs. The reaction mixture was then cooled and separated from solid catalyst by filtration and analysed by gas chromatography (Shimadzu GC RIA) using carbowax column and flame ionisation detector (FID). The identify of the product was confirmed by GC mass spectroscopy (Shimadzu GCMS-QP 2000A) using standard compounds.

The conversion of napthalene was 6.8%

The conversion of β naphthol was 3.8%

The other side products were napthaquinone 1.7%, pthalic anhydride 0.3% and α naphthol 0.85%.

EXAMPLE-5

In a 250 ml 4 necked flask fitted with stirrer, condenser, thermometer, addition funnel in an electrically heated oil bath was charged with 1.5 g of solid copper tetra deca chloro pthalocyanine zeolite catalyst, methanol 150 ml (118 g) and napthalene 12.8 g, hydrogen peroxide 13.6 ml (28%) (3.808 g) was slowly added dropwise at 50° C. to the reaction mixture under stirring in 15 minutes. The reaction continued at 85° C. for 5 hrs. The reaction mixture was then cooled and separated from solid catalyst by filtration and analysed by gas chromatography (Shimadzu GC RIA) using carbowax column and flame ionisation detecter (FID). The identify of the product was confirmed by GC mass spectroscopy (Shimadzu GCMS-QP 2000A) using standard compounds.

The conversion of napthalene was 14%

The conversion of β naphthol was 4%

The other side products were napthaquinone 1.40%, pthalic anhydride 6% and α naphthol 1%.

We claim:

1. A process for the hydroxylation of naphthalene to α and β naphthols which comprises reacting naphthalene with hydrogen peroxide in the presence of a solid catalyst containing an organotransition metal complex selected from halophthalocyanines, metal nitrophthalocyanines metal cyano-phthalocyanines, and mixtures thereof at a temperature in the range of 20° C. to 85° C. and isolating the naphthols formed by conventional methods.

2. A process as claimed in claim 1, wherein the transition metal in the organotransition complex is selected from iron, cobalt, copper, chromium, manganese or mixtures thereof.

3. A process as claimed in claim 1, wherein some or all of the hydrogen atoms of said organotransition metal complex have been substituted by one of more electron withdrawing groups chosen from the group consisting of the halogens, the nitro group, the cyano group and mixtures thereof.

4. A process as claimed in claim 1, wherein the oxidation reaction is carried out in the presence of a solvent chosen from the group consisting of acetonitrile, methanol, butanol, cyclohexane and acetone.

5. A process as claimed in claim 1, wherein the organotransition metal complex is encapsulated in a solid matrix selected from inorganic oxides chosen from the group consisting of one or more of silica, alumina, aluminosilicates, molecular sieves, and organic polymer.

* * * * *